US010456291B2

United States Patent
Strong et al.

(10) Patent No.: US 10,456,291 B2
(45) Date of Patent: *Oct. 29, 2019

(54) METHOD OF PROFILE HEATSEALING

(71) Applicant: The Procter & Gamble Company, Cincinnati, OH (US)

(72) Inventors: Kevin Charles Strong, Loveland, OH (US); Robert Clark Avery, Jr., Mason, OH (US); Evan Joseph Durling, West Chester, OH (US); Christian Giuliani, Pineto (IT)

(73) Assignee: The Procter & Gamble Company, Cincinnati, OH (US)

( * ) Notice: Subject to any disclaimer, the term of this patent is extended or adjusted under 35 U.S.C. 154(b) by 50 days.

This patent is subject to a terminal disclaimer.

(21) Appl. No.: 15/493,702

(22) Filed: Apr. 21, 2017

(65) Prior Publication Data

US 2017/0224457 A1   Aug. 10, 2017

Related U.S. Application Data

(63) Continuation of application No. 14/573,362, filed on Dec. 17, 2014, now Pat. No. 9,649,219.

(Continued)

(51) Int. Cl.
*A61F 6/08* (2006.01)
*B32B 37/06* (2006.01)
*B32B 37/18* (2006.01)
*B32B 38/00* (2006.01)
*A61F 2/00* (2006.01)
*A61F 5/455* (2006.01)

(52) U.S. Cl.
CPC ............... *A61F 6/08* (2013.01); *A61F 2/005* (2013.01); *A61F 5/4553* (2013.01); *B32B 37/06* (2013.01); *B32B 37/18* (2013.01); *B32B 38/0004* (2013.01); *B32B 38/0012* (2013.01); *A61F 2210/0066* (2013.01); *A61F 2230/001* (2013.01); *A61F 2240/001* (2013.01); *A61F 2250/0069* (2013.01); *B32B 2535/00* (2013.01); *Y10T 156/1028* (2015.01)

(58) Field of Classification Search
None
See application file for complete search history.

(56) References Cited

U.S. PATENT DOCUMENTS 4,019,498 A    4/1977  Hawtrey et al.
4,624,668 A *  11/1986  Siegers ............... A61F 13/2085
                                          604/358

(Continued)

FOREIGN PATENT DOCUMENTS

JP    H02-069695    9/1988
JP    H03-054635    8/1991

OTHER PUBLICATIONS

PCT International Search Report, PCT/US2014/070622, dated Mar. 11, 2015, 6 pages.

*Primary Examiner* — Barbara J Musser
(74) *Attorney, Agent, or Firm* — William E. Gallagher; Andres E. Velarde

(57) ABSTRACT

This application relates to a method of covering a pessary device for relief of female incontinence with an overwrap. More particularly, the present invention relates to methods of conforming the overwrap to the pessary device using a sealing mechanism.

15 Claims, 9 Drawing Sheets

Related U.S. Application Data

(60) Provisional application No. 61/919,171, filed on Dec. 20, 2013.

(56) References Cited

U.S. PATENT DOCUMENTS

| | | |
|---|---|---|
| 5,458,592 A | 10/1995 | Abuto et al. |
| 2002/0120243 A1 | 8/2002 | Kraemer et al. |
| 2003/0233742 A1* | 12/2003 | Jones ................ A61F 13/2085 28/118 |
| 2004/0259707 A1* | 12/2004 | Lochte .............. A61F 13/15699 492/30 |
| 2010/0130953 A1 | 5/2010 | Fung et al. |
| 2012/0259166 A1 | 10/2012 | Karapasha |

* cited by examiner

METHOD OF PROFILE HEATSEALING

This application is a divisional of U.S. application Ser. No. 14/573,362 filed Dec. 17, 2014, now U.S. Pat. No. 9,649,219, which claims priority to U.S. Provisional Application 61/919,172 filed Dec. 20, 2013.

FIELD OF INVENTION

This application relates to a method of covering a pessary device for relief of female incontinence with an overwrap. More particularly, the present invention relates to methods of conforming the overwrap to the pessary device with profile heat sealing.

BACKGROUND OF THE INVENTION

Urinary incontinence, in which the ordinary bodily muscle functions fail to prevent unintended leakage of urine, is a common malady among women, particularly older women. It is estimated that up to 50% of women occasionally leak urine involuntarily, and that approximately 25% of women will seek medical advice at some point in order to deal with the problem. Stress incontinence, the most common type of urinary incontinence, refers to the involuntary loss of urine resulting from abdominal pressure rise, occurring during exercise, coughing, sneezing, laughing, etc. When stress incontinence occurs, it is usually the result of the abnormal descent of the urethra and bladder neck below the level of the pelvic floor. Many women wear sanitary napkins or diapers in order to deal with incontinence, and some women resort to surgical procedures.

Pessary devices are known to help relieve involuntary urination in a female. Such pessary devices can be uncomfortable for a user during insertion and/or removal. Depending on the surface properties of the material, the pessary device may require additional force to remove the pessary device.

As such, there remains a need for a pessary device with improved comfort during use. One way to improve comfort is to wrap the device with an overwrap which becomes the contact layer of the device with the body. The overwrap should conform to the pessary device for improved comfort upon insertion, use, and removal. Conforming the overwrap to the pessary device minimizes the size of the wrapped pessary device. As such, there remains a need for a method to conform the overwrap to the pessary device.

Further, there remains a need for a pessary device with improved comfort during the removal process.

SUMMARY OF THE INVENTION

A method of conforming an overwrap to a pessary device is disclosed. The method includes providing a pessary device comprising a longitudinal axis, a transverse axis, and an outer surface; providing an overwrap; placing the pessary device in contact with the overwrap, wherein the overwrap covers at least a portion of the pessary device outer surface area; contacting the overwrap with a sealing mechanism, joining the overwrap to itself on the opposing side of the device which forms part of the final overwrap; and removing the sealing mechanism.

A method of conforming an overwrap to a pessary device is further disclosed. The method includes providing a pessary device comprising a longitudinal axis, a transverse axis, and an outer surface; providing an overwrap; placing the pessary device in contact with the overwrap, wherein the overwrap covers at least a portion of the pessary device outer surface area; and manipulating the overwrap to conform to the pessary device using a profile seal. Manipulating the overwrap to conform to the pessary device using a profile seal further includes placing a portion of the overwrap under tension, contacting the overwrap with a sealing mechanism, joining the overwrap to itself on the opposing side of the device which forms part of the final overwrap, and removing the sealing mechanism.

A method of conforming an overwrap to a pessary device is further disclosed. The method includes providing a pessary device comprising a longitudinal axis, a transverse axis, and an outer surface; providing an overwrap; placing the pessary device in contact with the overwrap; and contacting the overwrap with a sealing mechanism, joining the overwrap to itself on the opposing side of the pessary device.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1A:
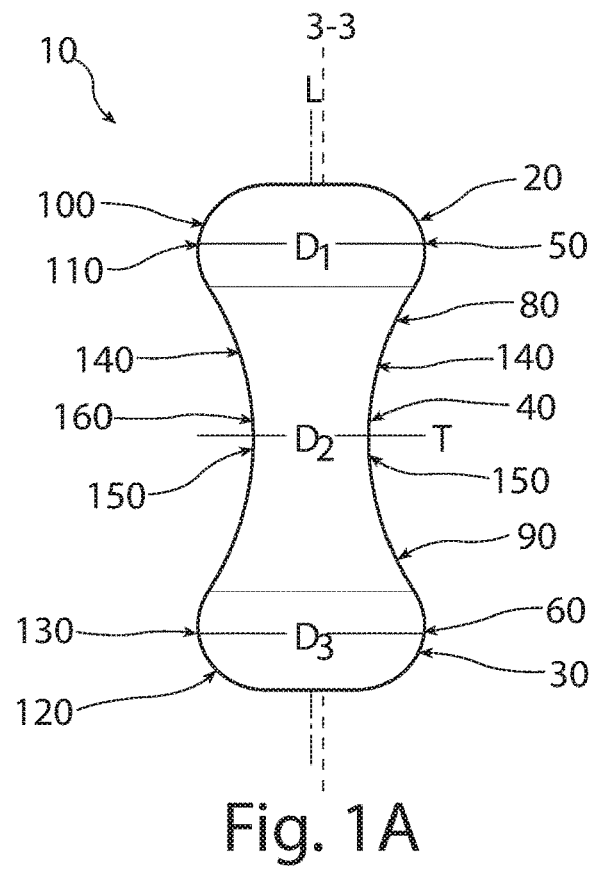
FIG. 1A is a side view of a pessary device.

As used herein, "applicator" refers to a device or implement that facilitates the insertion of the pessary device into an external orifice of a mammal. Exemplary applicators include telescoping, tube and plunger, and compact applicators.

As used herein, the term "conforming" or "conform" refers to making the overwrap similar to the outer surface of the pessary device such that at least about 30 percent to about 99 percent of the outer surface of the pessary device is in direct contact with the overwrap, such as, for example, 30 percent, 35 percent, 40 percent, 45 percent, 50 percent, 55 percent, 60 percent, 65 percent, 70 percent, 75 percent, 80 percent, 85 percent, 90 percent, and/or 95 percent.

The term "joined" or "attached" as used herein, encompasses configurations in which a first element is directly secured to a second element by affixing the first element directly to the second element, configurations in which the first element is indirectly secured to the second element by affixing the first element to intermediate member(s) which in turn are affixed to the second element, and configurations in which first element is integral with second element, i.e., first element is essentially part of the second element.

As used herein, the term "non-expandable" refers to devices that do not expand prior to or during use, such as, for example, devices that do not increase in size or volume prior to or during use. For example, non-expandable devices have a diameter and/or volume that does not increase. In contrast, "expandable" as used herein, refers to devices that do increase in size or volume prior to or during use, such as, for example, devices that increase in diameter and/or length, absorb fluid into a fibrous or absorbent gelling material structure, or otherwise change from a first size or volume to a second size or volume, such as, for example, by inflation, absorption, mechanically, or by other means. Insubstantial changes to a non-expandable device as a result of any thermal expansion that could occur at body temperatures are not considered "expansion."

A "pessary device" or more particularly an "incontinence pessary device" as used herein refers to devices specifically designed, configured, and/or adapted for placement into a vagina in order to reduce the occurrence and/or severity of female urinary incontinence. A "pessary device" can include any type of substantially non-absorbent structure for the purpose of reducing urine leakage and/or supporting a prolapsed uterus and/or bladder. A pessary device does not include a menstrual tampon.

As used herein, the term "vaginal canal" refers to the internal genitalia of the human female in the pudendal region of the body. The terms "vaginal canal" or "within the vagina" as used herein are intended to refer to the space located between the introitus of the vagina (sometimes referred to as the sphincter of the vagina) and the cervix.

The present invention is directed to a method of conforming an overwrap to a pessary device. The pessary device is placed in contact with an overwrap, wherein the overwrap covers at least a portion of the pessary device outer surface area. The overwrap may be formed from one continuous piece or may be formed by two pieces in contact with opposing sides of the pessary device. The overwrap is manipulated to conform to the shape of the pessary device using profile heat sealing.

The pessary device includes an upper portion, a lower portion, a middle portion, a pressure region of the upper portion, a pressure region of the lower portion, a maximum diameter, a minimum diameter, a slope extending from the upper portion to the middle portion, a slope from the middle portion to the lower portion, a longitudinal axis, and a transverse axis. The pessary device can be symmetric about the longitudinal axis, including for example, wherein the base is circular and symmetric about the longitudinal axis. The pessary device can have outer wall and an interior defined by inner walls that is hollow in region. The hollow region can be provided at one or both ends. In addition, the pessary device can have a portion of the interior that is solid. The pessary device does not change in size during the usage experience, that is, the pessary device is the same size and diameter prior to insertion by the user as well as during use and removal.

The pessary device can be a unitary construction. For example, the pessary device can include a continuous outer shell that defines the entire exterior surface of the pessary device. The outer shell can be smooth or textured. The outer shell may be permeable to fluid, such as, for example, by the inclusion of holes, pores, or other suitable external openings. Alternatively, the outer shell can be impermeable to fluid such that fluid cannot enter the device. In addition, the pessary device can include an external opening in the top and/or base. The pessary device can include an external opening in the top and/or base and the outer shell is not permeable to fluid such that fluid cannot enter the device except through the external opening in the top and/or base. The external opening in the top and or base may have external opening to the interior engaging members. The engaging members can be triangles, half circles, quarter circles, and/or geometric shapes with points. The engaging members can engage with the overwrap. Suitable pessary devices are typically smaller in size than conventional pessary devices. For example, the pessary devices have a maximum diameter, a length, and/or a volume that is smaller or less than that of conventional pessary devices.

The pessary device is covered by an overwrap. The overwrap can be non-absorbent or absorbent and can include any suitable material, such as, for example, a fibrous nonwoven material comprising natural, synthetic, or a blend of natural and synthetic fibers. Suitable synthetic fibers can include, e.g., fibers such as polyester, polyolefin, nylon, polypropylene, polyethylene, polyacrylic, cellulose acetate, polyhydroxyalkanoates, aliphatic ester polycondensates, bicomponent fibers and/or mixtures thereof. Natural fibers can include, e.g., rayon and those commonly known to be non-synthetic and of natural origin such as cotton. The fibers can have any suitable cross-sectional shape, such as, e.g., round, tri-lobal, multi-lobal, delta, hollow, ribbon-shaped, and/or any other suitable shape, or mixtures thereof. Fibers with any suitable diameter can be used, such as, e.g., from about 0.5 to about 50 microns, such as, e.g., from about 1 to about 30 microns, such as, e.g., from about 10 to about 25 microns. Fiber diameter can be determined using any suitable means; however, for non-round fibers, diameter can typically be determined by reference to the diameter of a fiber with the same cross-sectional area as the non-round fiber.

The overwrap is manipulated to conform to the pessary device by profile sealing. Profile sealing may involve the following steps: placing a portion of the overwrap under tension, contacting the overwrap with a heat seal or form of adhesive, joining the overwrap to another material forming on the opposing side of the device which forms part of the final overwrap or joining the overwrap to itself on the opposing side of the device, removing the heat seal, and trimming the overwrap. In an embodiment, the overwrap is placed under tension prior to contacting the pessary device. The overwrap may comprise one continuous piece that enrobes the pessary device. The overwrap may comprise two individual pieces placed above and below the device. In an embodiment wherein the overwrap comprises two pieces, one or both pieces may be placed under tension. In an embodiment wherein the overwrap comprises two pieces under tension, the tension may be the same for both pieces or may be different such that a first piece of overwrap may be under greater tension than a second piece of overwrap.

In an embodiment, a portion of the overwrap is preformed. Pre-forming may include, for example, a pre stretching step and a molding step. Pre-forming may be done integral to the seal or can be done as a separate step prior to the seal to form a pocket in the overwrap material.

The level of tension required may depend on the irregularity of the cross section of the pessary device or three dimensional object. A higher tension is required to conform to the highest delta of the cross section. Minimal tension (approximately 1 g) is required to control the web. Maximum tension could be as high as, but not limited to, 1000 g (10 g/mm of web width/web).

The tension may increase past the yield point when the material is fully conformed to the device. Material delivery tension may be below the yield point. Web tension, in part, determines how tight the overwrap is to the device. Other factors determining the tightness of the overwrap include proximity of the seal to the device.

Contacting the overwrap with a heat seal may include contacting a portion of one side of the overwrap, both sides of the overwrap, or the entire portion of the overwrap that will contact the pessary device. Overwrap material may extend beyond the heat seal in any given direction.

In an embodiment, the overwrap may be joined to itself or to a second piece of overwrap such that the device is located between the two joined portions of overwrap. For example, one portion of overwrap can be joined to an opposed portion of the overwrap using any suitable adhesive or heat pressure bonding means. Joining can create continuous bonding points along the length of attachment or it can create non-continuous bonding points at discrete intervals. The overwraps may be joined by heat sealing. Heat sealing includes thermally bonding, fusion bonding, or any other suitable means for joining such materials. Heat sealing may create profile bonds that outline the shape of the device. The profile bonds may have a point diameter between 0.5 mm to 2 mm, such as, for example, 1 mm. Profile seal bond point spacing may be between 0.5 mm and 1.5 mm, such as, for example, 1 mm. Bond points are made along the complete side length of the pessary device and extend up to, but not limited to, 50 mm beyond the end of the device. The seal is maintained between 0.25 mm and 1 mm from the device.

In an embodiment, the profile seal bond points run along at least 35% of the perimeter of the device. In an embodiment, the profile seal maintains the device within the overwrap such that the device cannot be removed from the overwrap without breaking at least one bond point of the profile seal. In an embodiment wherein the device is in the form of a cylinder or bullet, the device may be removed without breaking a profile seal bond.

Seal temperatures are above the melting temp of the overwrap material at about 130° C. to 200° C. Sealing temperatures may vary depending on time and pressure. The Seal strength must be adequate to maintain a bond under the residual overwrap tension when the product is released from the process.

It has been found that, in profile heat sealing, to eliminate burn through due to "tenting" of the overwrap at the point of the seal, an additional component may be used to conform the overwrap around the pessary device bringing the two layers together prior to or at the same time the heated tool contacts the material to join the two layers. This additional component can be integral to the heat seal tooling or a separate part. The additional component maintains overwrap to overwrap contact while the heat is applied. The additional component maintains its surface temperature below the melting point of the overwrap material.

After being joined, the overwrap may be trimmed to between 0.5 mm to 2 mm outside the seal created by the joining process along the longitudinal length of the device, such as, for example, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm or 1.9 mm. Applicants have found that leaving a length between 0.5 mm to 2 mm outside of the seal along the profile bonds or seal points creates a soft edge making the product comfortable during insertion and removal.

In an embodiment, an external sealed flap between 0.5 mm and 3 mm in width may be found at each end of the profile seal. The external sealed flap may comprise one or more bond points. In an embodiment, the external sealed flap may comprise a plurality of bond points that form a geometric pattern such as, for example, a square. Applicants have found that by cutting outside of the bond points, a soft edge is maintained on the product.

In an embodiment, the sealing process forms an end seal at each end. The end seals may aid in collecting and pushing the overhanging overwrap into the device at both ends. This end seal is located about 4 mm (−3 mm+6 mm) from the end of the pessary device. The end seal consists of individual bond seal points totaling approximately 1 cm in length and width. The bond points may be the same dimensions and spacing as the profiled seal.

Figure 1B:
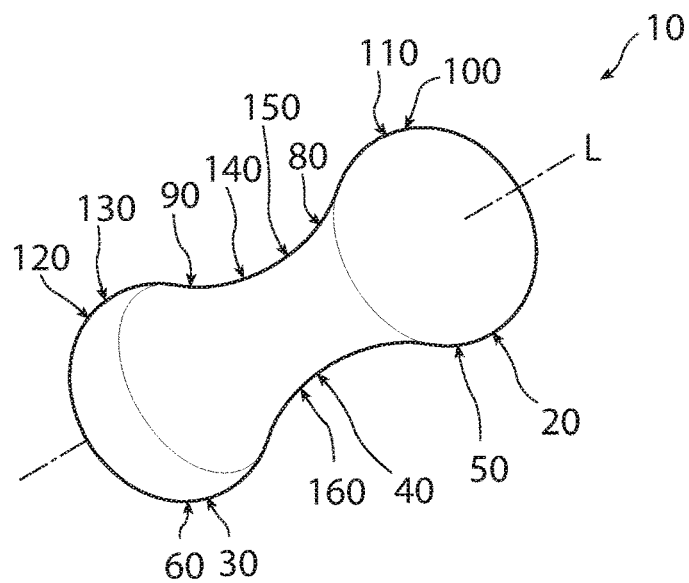
FIG. 1B is a perspective view of the pessary device of FIG. 1A.

An exemplary pessary device 10 is shown in FIGS. 1A and 1B. The pessary device 10 includes an upper portion 20, a lower portion 30, a middle portion 40, a pressure region 50 of the upper portion 20, a pressure region 60 of the lower portion 30, a maximum diameter $D_1$, a minimum diameter $D_2$, a slope 80 extending from the upper portion 20 to the middle portion 40, a slope 90 from the middle portion 40 to the lower portion 30, a longitudinal axis (L) and a transverse axis (T). As shown in FIGS. 1A and 1B, the pessary device 10 can have a top 100 that includes a convex portion 110, a base 120 that includes a convex portion 130, and sides 140 that include concave portions 150. The pessary device can be symmetric about the longitudinal axis, including for example, wherein the base is circular and symmetric about the longitudinal axis. The pessary device can include a third diameter $D_3$ that is greater than minimum diameter $D_2$, and convex portion 110 can be aligned with maximum diameter $D_1$ to provide pressure region 50, and convex portion 130 can be aligned with maximum diameter $D_1$ to provide pressure region 60. In addition, concave portion 150 can be aligned with minimum diameter $D_2$ to form flexile region 160.

Figure 2A:
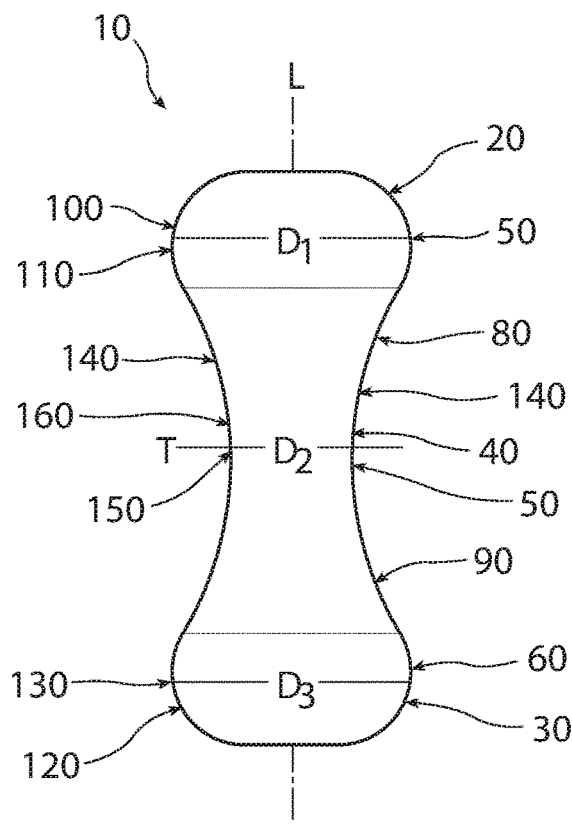
FIG. 2A is a side view of a pessary device.
Figure 2B:
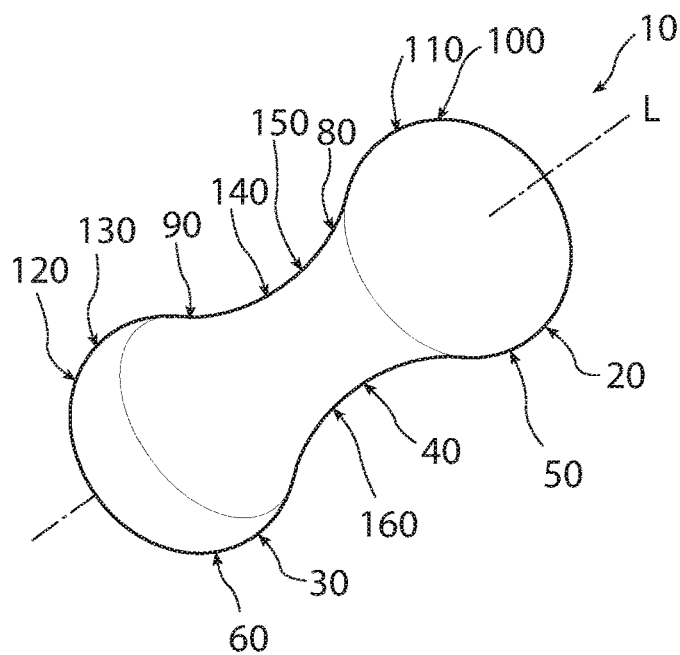
FIG. 2B is a perspective view of the pessary device of FIG. 2B.

FIGS. 2A and 2B show a pessary device 10. The pessary device 10 includes an upper portion 20, a lower portion 30, a middle portion 40, a pressure region 50 of the upper portion 20, a pressure region 60 of the lower portion 30, a maximum diameter $D_1$, a minimum diameter $D_2$, a slope 80 extending from the upper portion 20 to the middle portion 40, a slope 90 from the middle portion 40 to the lower portion 30, a longitudinal axis (L) and a transverse axis (T). As shown in FIGS. 2A and 2B, the pessary device 10 can have a top 100 that includes a convex portion 110, a base 120 that includes a convex portion 130, and sides 140 that include concave portions 150. The pessary device shown in FIGS. 2A and 2B has an upper slope 80 that is greater than the upper slope 80 of the pessary device shown in FIGS. 1A and 1B. As shown in FIGS. 2A and 2B, pessary device 10 can include flexile region 160. In addition, the pessary device shown in FIGS. 2A and 2B has a lower slope 90 that is greater than the lower slope 90 of the pessary device shown in FIGS. 1A and 1B.

Figure 3:
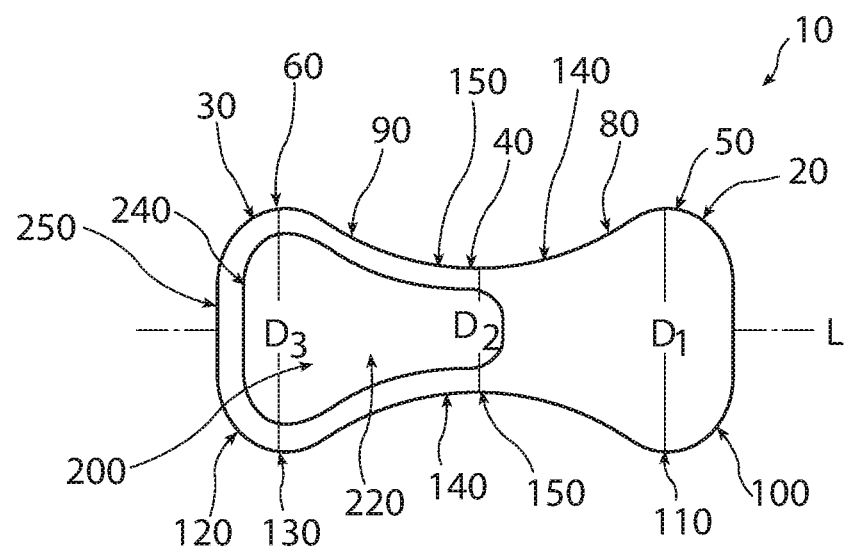
FIG. 3 is a cross-section view of a pessary device.

FIG. 3 shows a pessary device 10 take along line 3-3 of FIG. 1. The pessary device 10 includes an upper portion 20, a lower portion 30, a middle portion 40, a pressure region 50 of the upper portion 20, a pressure region 60 of the lower portion 30, a maximum diameter $D_1$, a minimum diameter $D_2$, a slope 80 extending from the upper portion 20 to the middle portion 40, a slope 90 from the middle portion 40 to the lower portion 30, and a longitudinal axis (L). As shown in FIG. 3, the pessary device 10 can have a top 100 that includes a convex portion 110, a base 120 that includes a convex portion 130, and sides 140 that include concave portions 150. As shown in FIG. 3, the pessary device 10 can have outer wall 250 and an interior 200 defined by inner walls 240 that is hollow in region 220. The hollow region 220 can be provided at one or both ends. In addition, the pessary device 10 can have a portion of the interior 200 that is solid.

Figure 4:
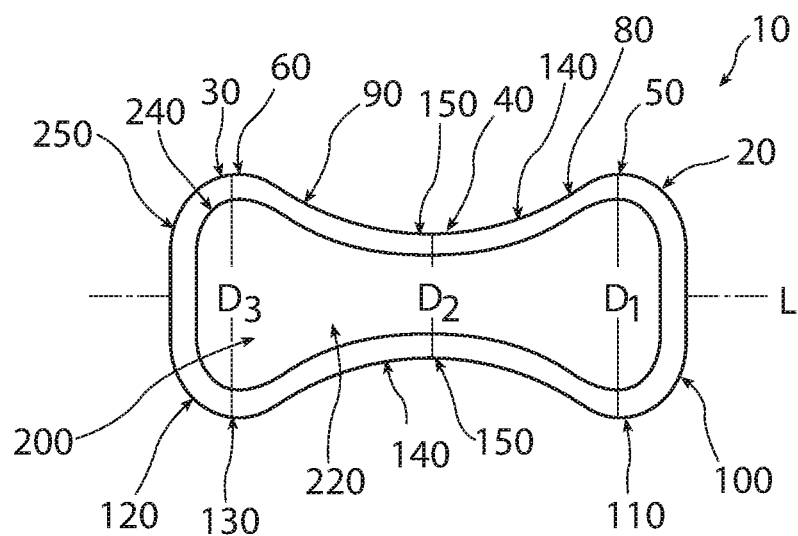
FIG. 4 is a cross-section view of a pessary device.

FIG. 4 shows a pessary device 10. The pessary device 10 includes an upper portion 20, a lower portion 30, a middle portion 40, a pressure region 50 of the upper portion 20, a pressure region 60 of the lower portion 30, a maximum diameter $D_1$, a minimum diameter $D_2$, a slope 80 extending from the upper portion 20 to the middle portion 40, a slope 90 from the middle portion 40 to the lower portion 30, and a longitudinal axis (L) crossing both ends. As shown in FIG. 4, the pessary device 10 can have a top 100 that includes a convex portion 110, a base 120 that includes a convex portion 130, and sides 140 that include concave portions 150. As shown in FIG. 4, the pessary device 10 can have an interior 200 that is hollow. The pessary device has inner walls 240 that define interior 200 and hollow region 220. In addition, the inner walls 240 can have the same or a similar profile as the outer walls 250.

Figure 5:
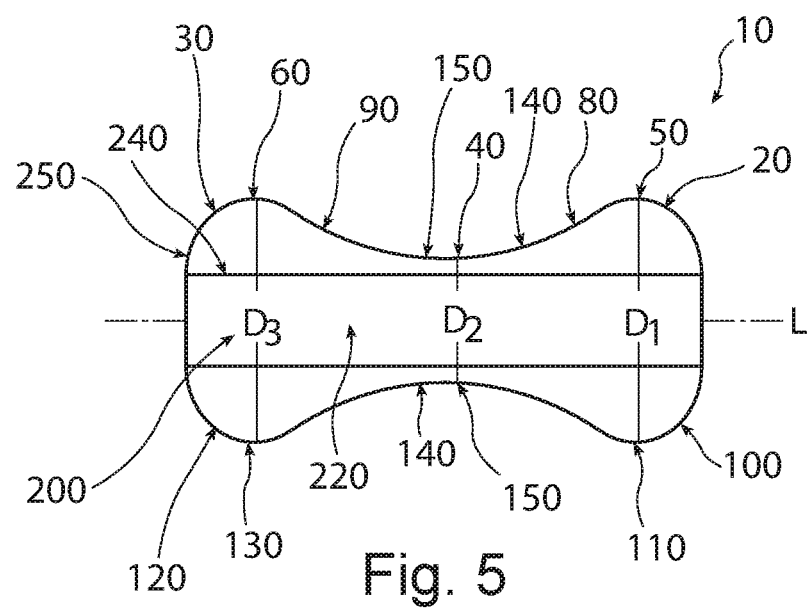
FIG. 5 is a cross-section view of a pessary device.

FIG. 5 shows a pessary device 10. The pessary device 10 includes an upper portion 20, a lower portion 30, a middle portion 40, a pressure region 50 of the upper portion 20, a pressure region 60 of the lower portion 30, a maximum diameter $D_1$, a minimum diameter $D_2$, a slope 80 extending from the upper portion 20 to the middle portion 40, a slope 90 from the middle portion 40 to the lower portion 30, and a longitudinal axis (L) crossing both ends. As shown in FIG. 5, the pessary device 10 can have a top 100 that includes a convex portion 110, a base 120 that includes a convex portion 130, and sides 140 that include concave portions 150. As shown in FIG. 5, the pessary device 10 has an interior 200 that is hollow. The pessary device has inner walls 240 that define interior 200 and hollow region 220. The hollow region 220 can have a first profile defined by inner walls 240 and a different profile defined by outer walls 250, such as, for example, where the hollow region 220 is in the form of a tube.

Figure 6:
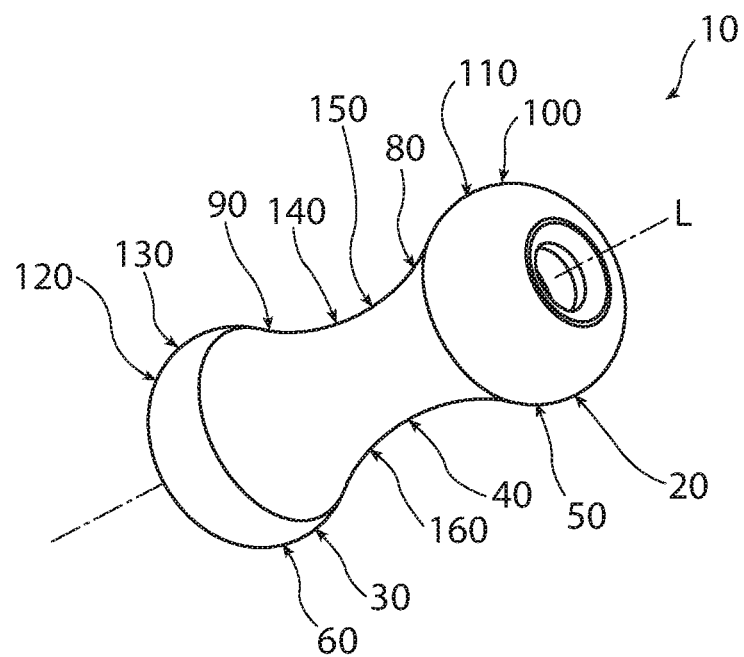
FIG. 6 is a perspective view of a pessary device.

FIG. 6 shows a pessary device 10. The pessary device 10 includes an upper portion 20, a lower portion 30, a middle portion 40, a pressure region 50 of the upper portion 20, a pressure region 60 of the lower portion 30, a slope 80 extending from the upper portion 20 to the middle portion 40, a slope 90 from the middle portion 40 to the lower portion 30, and a longitudinal axis (L). As shown in FIG. 6, the pessary device 10 can have a top 100 that includes a convex portion 110, a base 120 that includes a convex portion 130, and sides 140 that include concave portions 150. The pessary device can also have a flexile region 160. The pessary device 10 can have an interior 200 that is hollow. In addition, as shown in FIG. 6, the pessary device 10 can have an opening on one or more of top 100 and/or on base 120.

Figure 7:
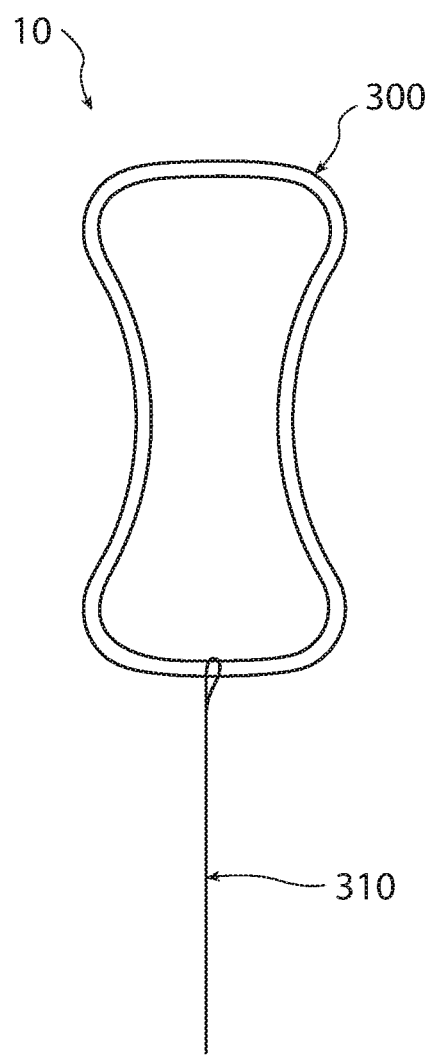
FIG. 7 is a side view of a pessary device.

The pessary device 10 can include an overwrap 300 and/or a withdrawal member 310, such as, for example, as shown in FIG. 7. In addition, FIG. 7 shows that withdrawal member 310 can be attached to overwrap 300.

Figure 8:
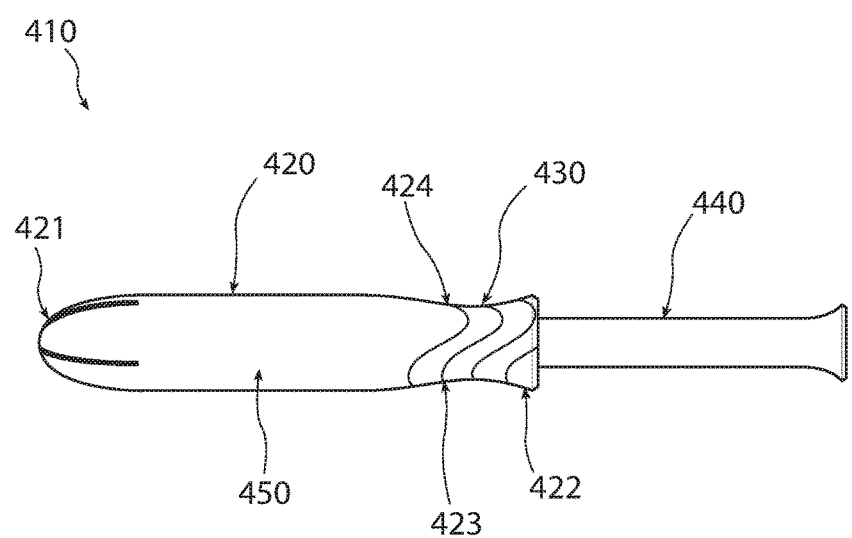
FIG. 8 is a side view of a pessary applicator, housing the pessary of FIG. 1.

The pessary device can be inserted in any suitable manner, such as, for example, using an applicator. FIG. 8 shows an applicator 410 that includes an insertion member 420 and a plunger 440. The insertion member 420 has an insertion end 421 and a withdrawal end 422 opposite the insertion end 421. The insertion member 420 also can include a barrel region 450 adapted to contain a pessary device, and a grip region 430 that can be an indentation region 424 provided opposite the insertion end 421, such as, e.g., proximal to the withdrawal end 422. The grip region 430 can include one or more grip elements 423.

Figure 9:
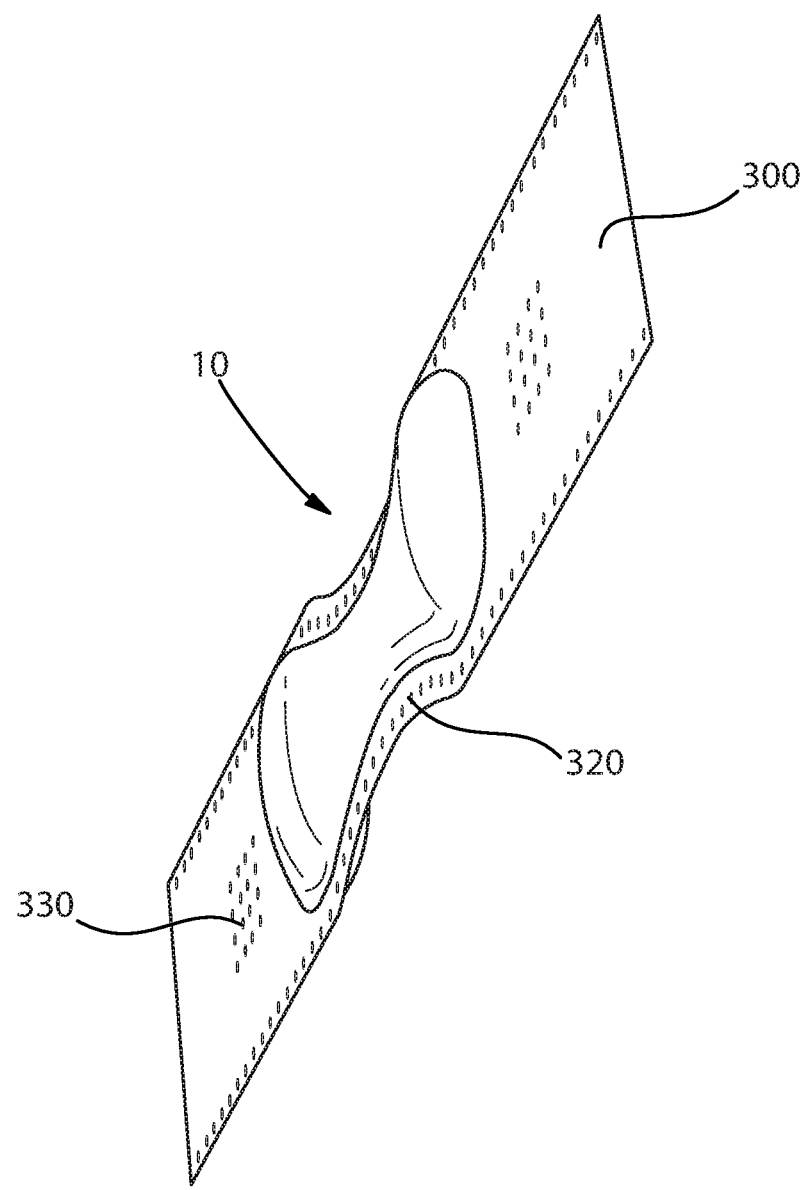
FIG. 9 is a perspective view of the pessary device with a profile seal.

FIG. 9 shows a pessary device 10 with an overwrap 300. The overwrap 300 conforms to the pessary device 10. The overwrap has been profile sealed. As shown in FIG. 9, bond points 320 are located on the sides of the device. Additional end seals 330 are located on each end of the pessary device 10.

Figure 10:
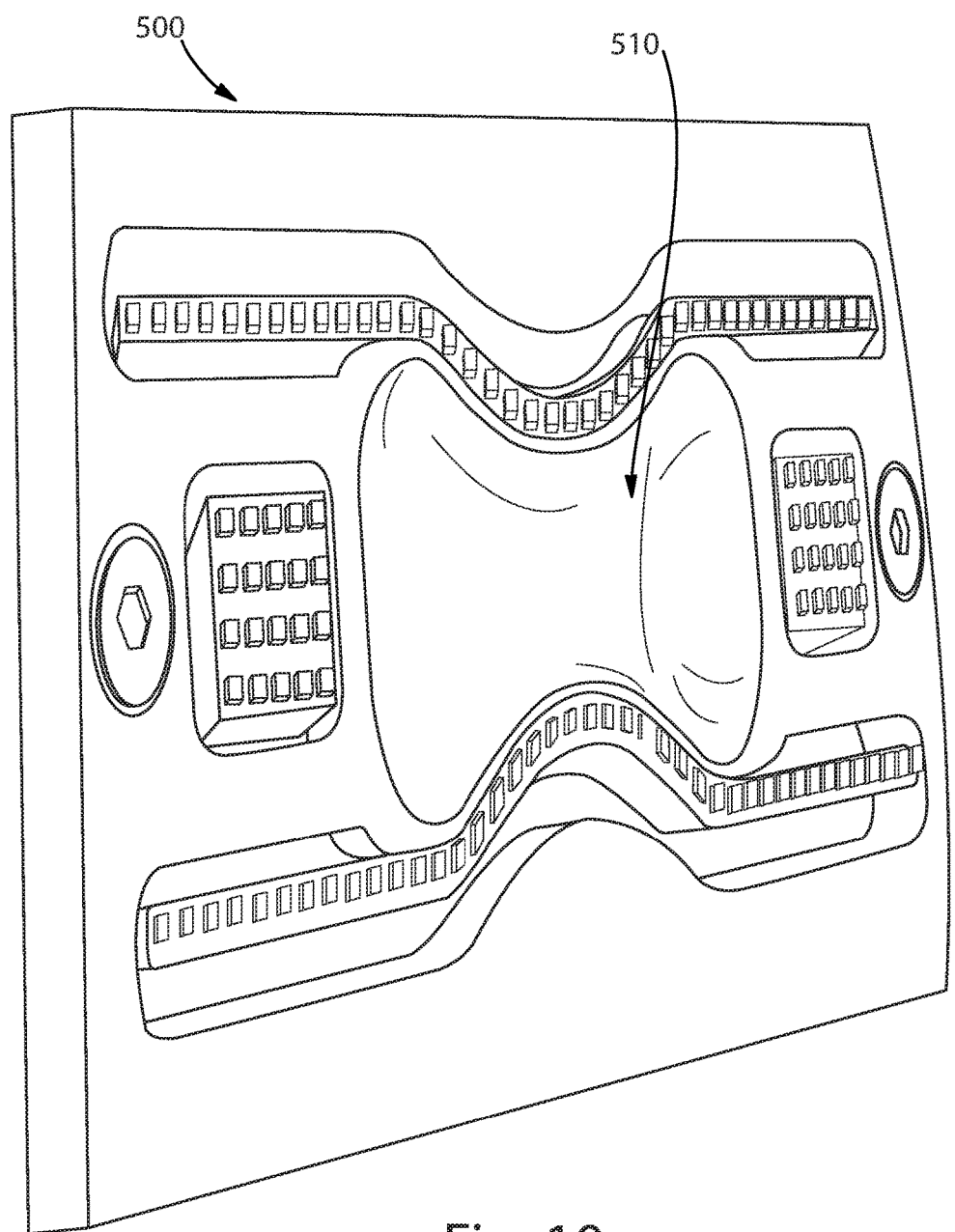
FIG. 10 is a perspective view of the profile seal tool.

FIG. 10 shows a profile sealing tool 500. The tool contains an additional component 510 that is capable of maintaining a temperature below the melt temperature of the overwrap.

Figure 11:
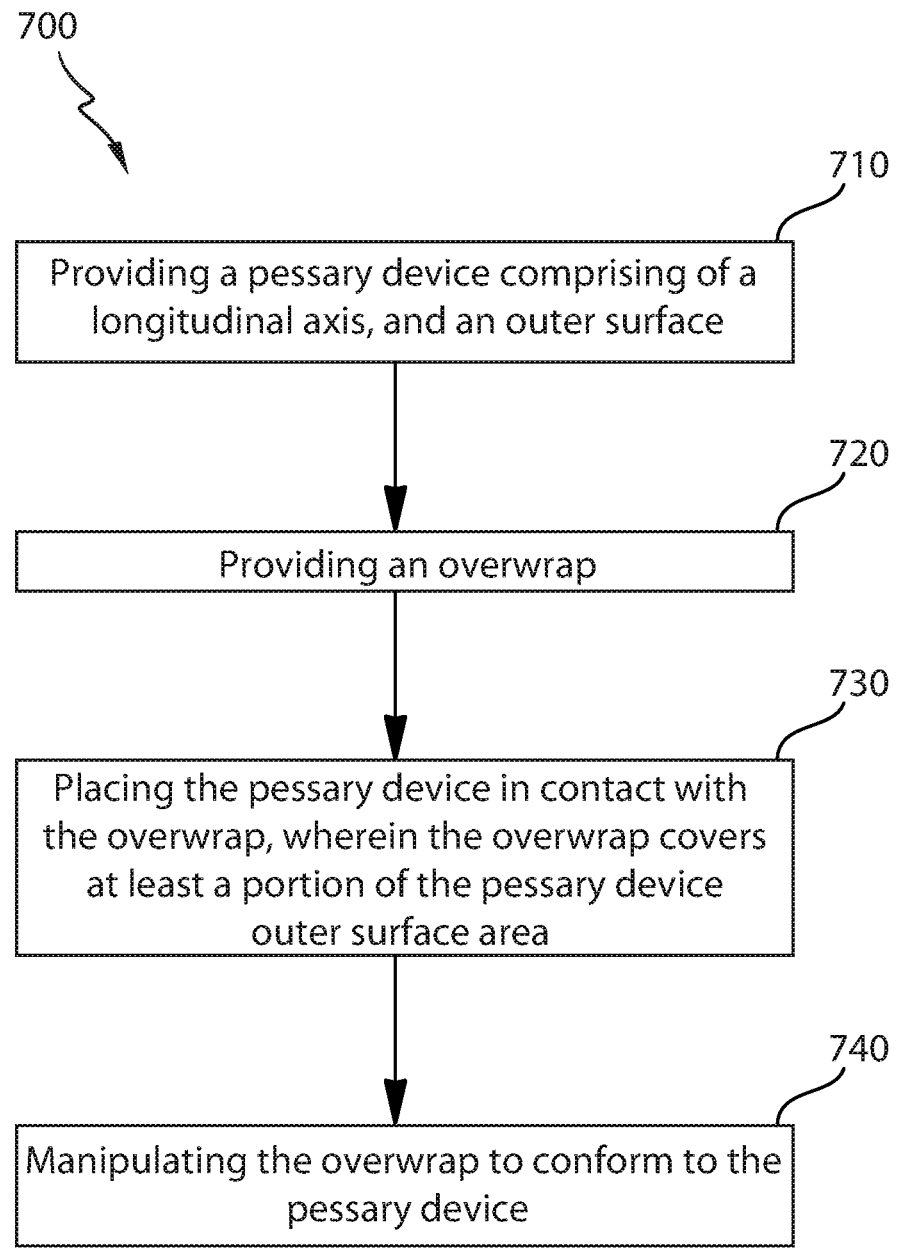
FIG. 11 is a flowchart describing the method of conforming an overwrap to a pessary device.

FIG. 11 a flowchart describing the method of conforming an overwrap to a pessary device 700. The method includes providing a pessary device comprising a longitudinal axis, and an outer surface 710. The method further includes providing an overwrap 720. The overwrap may be made into a hollow structure. The pessary device is placed in contact with the overwrap so that the overwrap covers at least a portion of the pessary device outer surface area 730.

The method further includes manipulating the overwrap to conform to the pessary device 740. Manipulating the overwrap may include profile sealing the overwrap about the pessary device. The profile seal may join the overwrap to another material forming the overwrap on the opposing side of the device which forms part of the final overwrap or joining the overwrap to itself on the opposing side of the device.

Generally, the pessary device does not change in size during the usage experience, that is, the pessary device is the same size and diameter prior to insertion by the user as well as during use and removal. For example, the pessary device is not expandable or inflatable from its original size and the pessary device is not compressed for insertion into the user's body, nor is the pessary device compressed for withdrawal from the user's body. A portion or region of the pessary device can flex or be deformed, such as, for example, in the region having the minimum diameter, but the pessary device does not expand and returns to the original configuration after deformation. As such, the pessary device does not include any mechanical or other means that requires the user to change the size or shape of the pessary device during use, such as, for example, before or after insertion or prior to withdrawal. This provides for a pessary device that has a size upon withdrawal that is the same as the size during use, which can provide for improved comfort during use and withdrawal.

The pessary device can have a pressure region that has the maximum diameter of the pessary, such as, for example, at the base or at the top, that extends between the anterior vaginal wall and the posterior vaginal wall of a consumer to provide pressure on the urethra through the vaginal wall. In addition, the pessary device can have a second pressure region having an increased diameter as compared to the minimum diameter that can provide pressure on the urethra through the vaginal wall at a point apart from the first pressure region. The first pressure region and the second pressure region can be separated by any suitable distance, such as, for example, by at least about 5 mm, at least about 10 mm, at least about 15 mm, at least about 20 mm, at least about 25 mm, at least about 30 mm, at least about 35 mm, at least about 40 mm, at least about 45 mm, at least about 50 mm, or any other suitable distance.

The pessary device can have any suitable number of pressure regions, including for example, two pressure regions, such as, for example, four or fewer pressure regions, three or fewer pressure regions, two or fewer pressure regions, one pressure region, or any other suitable number of pressure regions.

The pressure region or regions can be any suitable shape, such as, for example, a convex shape that provides pressure to the vaginal wall, including, for example, a lobe or other protuberance. The pressure region or regions can have a substantially circular cross-section. The pessary device also can include a minimum diameter region that is a flexile region that can provide flexibility to the pessary device, such as, for example, by allowing bending or movement at the flexile region. The flexile region can be any suitable shape, such as, for example, concave, indented, or the like, and can have any suitable cross-section, such as, for example, a substantially circular cross-section. The pessary device can include a flexile region provided between two pressure regions.

Maximum pressure to the urethra and maximum urethral closure can be measured using any suitable method, such as, for example, by using the computational model described in U.S. Patent Appln. No. 2007/0027667. For example, a computation model simulating the human internal pelvic environment can be used. In certain embodiments, thirteen nodes on the urethra in the simulation that are both on the back wall toward the vagina and in the middle of the body on the sagittal plane can be chosen. The points should be spread even along the length of the urethra with the first point at the bottom edge of the urethra and the last point at the bladder neck. Node vs. time vs. Von Mises stress should be obtained using a suitable software program, such as, for example, LS-Prepost, for all chosen nodes. The data columns are then matched to determine the y position vs. time vs. Von Mises stress. Generally, only the data that is at the simulation end point should be selected and y-position vs. Von Mises is then plotted.

The flexile region, on the other hand, is more flexible than and provides less resistance than the pressure region. Addition of the flexile region can allow the pessary device to flex in the longitudinal direction as well at the lateral direction. For example, the pessary device can compress more than about 1 cm when measured under 0.5 psi when the force is applied from the top to the base along the longitudinal axis. In addition, or alternatively, the flexile region can provide a bending region that facilitates the pessary device bending from side to side.

The pessary device can be a unitary construction. For example, the pessary device can include a continuous outer shell that defines the entire exterior surface of the pessary device. The outer shell can be smooth or textured. The outer shell may be permeable to fluid, such as, for example, by the inclusion of holes, pores, or other suitable openings. Alternatively, the outer shell can be impermeable to fluid such that fluid cannot enter the device. In addition, the pessary device can include an opening in the top and/or base. The pessary device can include an opening in the top and/or base and the outer shell is not permeable to fluid such that fluid cannot enter the device except through the opening in the top and/or base.

Suitable pessary devices can be solid or can have a hollow interior or cavity. For hollow devices, the pessary device can have an outer periphery defining a total area of the device and an inner periphery defining an open area of the device. The open area can be any suitable size, such as, for example, between about 5% to about 95% of the total area, such as, for example, from about 10% to about 90% of the total area, from about 15% to about 85% of the total area, or from about 20% to about 80% of the total area. In addition, the pessary device also can have a wall thickness that is suitable to maintain the pessary configuration. The wall thickness can be greater than about 0.5 mm, such as for example, about 1 mm about 2 mm, about 3 mm, about 4 mm, about 5 mm, or greater. The wall thickness can be constant or varied along the length of the pessary device and/or around the circumference of the pessary device.

The pessary device can have any suitable shape having a varied diameter along the longitudinal axis, such as, for example, a shape having a varied diameter that is symmetrical with respect to the longitudinal axis, such as, for example, a teardrop, an apple, a pear, an hourglass, a waisted cylinder, a figure-8 shape, a peanut shape, a heart-shape, a light bulb shape, a bottle shape, a vase shape, or any other suitable shape. In addition, the shape can have a varied diameter and can be symmetrical with respect to both the longitudinal and lateral axis, such as, for example, an hourglass, a waisted cylinder, a figure-8 shape, a peanut shape, or any other suitable shape. Alternatively, the pessary device can have an asymmetrical shape, such as, for example, a B-shape or a P-shape. The pessary device can be symmetrical at one region and asymmetrical at another region, such as, for example, where the pessary device has a symmetrical pressure region and an asymmetrical flexile region. Generally, the pessary device can have a varying diameter that can provide varying pressure along the user's urethra. For example, the pessary device can have a convex portion that can correspond to the pressure region. In addition, the pessary device can have a minimum diameter region that can be a concave region. The concave region can correspond to the flexile region.

The pessary device can be hourglass shaped. For example, as shown in FIGS. 1-2, the pessary device can have upper and lower portions joined together by a waistline portion, with the upper and lower portions having diameters that are both greater than a diameter of the waistline portion such that the pessary device has a generally hourglass configuration. In this configuration, the upper portion of the pessary device can have a top and the lower portion of the pessary device can have a base, and the pessary device can have sloping upper and lower wall sections joining the top and the base with the waistline portion. In addition, the waistline portion can include the minimum diameter of the pessary device. The upper and lower portions can have generally coequal maximum diameters, or the upper and lower portions can have different maximum diameters, such as, for example, where the upper portion has a maximum diameter greater than the lower portion or where the lower portion has a maximum diameter greater than the upper portion.

Generally, the pessary device includes at least one maximum diameter and at least one minimum diameter, where the minimum diameter is smaller than the maximum diameter. The pessary device can include a first portion having a maximum diameter, a second portion having a maximum diameter, and a third portion that has a minimum diameter. The maximum diameter of the first portion and the maximum diameter of the second portion can be separated by a distance that is greater than about 10% of the length of the pessary device, such as, for example, by a distance greater than about 5 mm, greater than about 10 mm, greater than about 15 mm, greater than about 20 mm, greater than about 25 mm, greater than about 30 mm, greater than about 35 mm, greater than about 40 mm, greater than about 45 mm, or more. The pessary device can provide pressure at mid-urethra, the bladder neck, or both. In addition, the pessary device can provide higher pressure at the mid-urethra, the bladder neck, or both and provides lower pressure at the area between the mid-urethra and the bladder neck. For example, the pressure region can provide pressure at levels about 25% higher than the pressure provided by the flexile region, such as, for example, at levels about 30% higher, about 35% higher, about 40% higher, about 45% higher, about 50% higher, about 55% higher, about 60% higher, or more.

The pessary device can have a slope from the maximum diameter to the minimum diameter. Any suitable slope can be used, including for example, about 0.25 mm, about 0.5 mm, about 0.75 mm, about 1 mm, about 1.5 mm, about 2 mm, about 2.5 mm, about 3 mm, about 4 mm, about 5 mm, about 6 mm, about 7 mm, about 8 mm, or more, such as, for example, a slope from about 0.25 mm to about 5 mm, or a slope from about 0.5 mm to about 4 mm, or any other suitable range.

Suitable pessary devices are typically smaller in size than conventional pessary devices. For example, the pessary devices have a maximum diameter, a length, and/or a volume that is smaller or less than that of conventional pessary devices.

The pessary devices can have any suitable maximum diameter, such as, for example, a maximum diameter of less than 35 mm, such as, for example, less than 34 mm, less than 33 mm, less than 32 mm, less than 31 mm, less than 30 mm, less than 29 mm, less than 28 mm, less than 27 mm, less than 26 mm, less than 25 mm, less than 24 mm, less than 23 mm, less than 22 mm, less than 21 mm, less than 20 mm, less than 19 mm, less than 18 mm, less than 17 mm, less than 16 mm, less than 15 mm, less than 14 mm, less than 13 mm, less than 12 mm, less than 11 mm, or less than 10 mm, including, for example, a maximum diameter of from about 10 mm to about 35 mm, from about 10 mm to about 25 mm, from about 13 mm to about 25 mm, or from about 15 mm to about 22 mm. The maximum diameter or width is typically measured at the widest portion of the pessary device substantially perpendicular to the longitudinal axis.

The pessary devices can have any suitable minimum diameter that is smaller than the maximum diameter, including, for example, a minimum diameter from about 40% to about 95% of the maximum diameter, from about 40% to about 90% of the maximum diameter, from about 40% to about 85% of the maximum diameter, from about 40% to about 80% of the maximum diameter, from about 45% to about 75% of the maximum diameter, or from about 50% to about 70% of the maximum diameter, such as, for example, about 45% of the maximum diameter, about 50% of the maximum diameter, about 55% of the maximum diameter, about 60% of the maximum diameter, about 65% of the maximum diameter, or about 70% of the maximum diameter.

The pessary devices can have a minimum diameter from about 4 mm to about 28 mm, about 5 mm to about 20 mm, about 8 mm to about 20 mm, from about 8 mm to about 18 mm, or from about 8 mm to about 15 mm, such as, for example, about 8 mm, about 8.5 mm, about 9 mm, about 9.5 mm, about 10 mm, about 10.5 mm, about 11 mm, about 11.5 mm, about 12 mm, about 12.5 mm, about 13 mm, about 13.5 mm, about 14 mm, about 14.5 mm, about 15 mm, about 15.5 mm, about 16 mm, about 16.5 mm, about 17 mm, about 17.5 mm, about 18 mm, about 18.5 mm, about 19 mm, about 19.5 mm, or about 20 mm, or any other suitable minimum diameter. The minimum diameter or width is typically measured at the narrowest portion of the pessary device substantially perpendicular to the longitudinal axis.

The maximum diameter and the minimum diameter can be separated by any suitable distance, such as, for example, by about 5 mm, about 10 mm, about 15 mm, about 20 mm, about 25 mm, about 30 mm, about 35 mm, about 40 mm, about 45 mm, about 50 mm, or any other suitable distance.

The pessary devices can have any suitable length, such as, for example, a length from about 35 mm to about 60 mm, about 40 mm to about 55 mm, or about 40 mm to about 50 mm, such as, for example, a length about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, or about 50 mm. The length is typically measured substantially parallel to the longitudinal axis of the pessary device.

Generally, the pessary device can have a weight of less than about 10 grams, less than about 9 grams, less than about 8 grams, less than about 7 grams, less than about 6 grams, less than about 5 grams, less than about 4 grams, less than about 3 grams, less than about 2 grams, or about 1 gram, including for example, a weight of from about 1 gram to about 7 grams, or from about 2 grams to about 6 grams, or from about 3 grams to about 5 grams.

Pessary devices can be fabricated using any suitable materials and methods. For example, pessaries can be formed from polymeric materials, such as, for example, polycarbonate, polyester, polyethylene, polyacrylamide, polyformaldehyde, polymethylmethacrylate, polypropylene, polytetrafluoroethylene, polytrifluorochlorethylene, polyvinylchloride, polyurethane, nylon, silicone, or mixtures or blends thereof, or metallic materials.

Pessary devices can be formed in any suitable manner, such as, for example, using injection molding or other suitable methods of forming the pessary device.

The pessary device can be covered by an overwrap. The overwrap can be non-absorbent or absorbent and can include any suitable material, such as, for example, a fibrous nonwoven material comprising natural, synthetic, or a blend of natural and synthetic fibers. Suitable synthetic fibers can include, e.g., fibers such as polyester, polyolefin, nylon, polypropylene, polyethylene, polyacrylic, cellulose acetate, polyhydroxyalkanoates, aliphatic ester polycondensates, bicomponent fibers and/or mixtures thereof. Natural fibers can include, e.g., rayon and those commonly known to be non-synthetic and of natural origin such as cotton. The fibers can have any suitable cross-sectional shape, such as, e.g., round, tri-lobal, multi-lobal, delta, hollow, ribbon-shaped, and/or any other suitable shape, or mixtures thereof. Fibers with any suitable diameter can be used, such as, e.g., from about 0.5 to about 50 microns, such as, e.g., from about 1 to about 30 microns, such as, e.g., from about 10 to about 25 microns. Fiber diameter can be determined using any suitable means; however, for non-round fibers, diameter can typically be determined by reference to the diameter of a fiber with the same cross-sectional area as the non-round fiber.

The overwrap can be made by any number of suitable techniques and can have any suitable basis weight. Suitable techniques include, for example, carding, meltblowing, spunbonding, spunlacing, air laying, and the like. For example, the overwrap can be formed using bonding methods, such as, e.g., thermal, ultrasonic, resin, through-air bonding, hydroentangling, and/or needling. The basis weight of the overwrap can be any suitable weight, such as, e.g., from about 10 to about 60 grams per square meter (gsm), such as, e.g., from about 15 to about 30 gsm. In addition, the overwrap can be hydrophilic or hydrophobic. The overwrap may be elastic. The overwrap may be shrinkable when exposed to heat or infrared.

The overwrap can be joined to the pessary device by any variety of means. The overwrap can be joined to itself or to the pessary device. For example, one portion of overwrap can be joined to an opposed portion of the overwrap or to the pessary device using any suitable adhesive or heat pressure bonding means. Such adhesive can extend continuously along the length of attachment or it can be applied in a non-continuous fashion at discrete intervals. Heat bonding includes thermally bonding, fusion bonding, or any other suitable means for joining such materials.

The overwrap may be joined to itself to form a hollow structure. The hollow structure may be in the form of any multi-dimensional geometric structure such as, for example, a cylinder, tunnel, tube, cube, and/or a pyramid. As described above, joining may occur using a profile seal.

At least a portion of the pessary device may be placed inside the overwrap hollow structure. The overwrap hollow structure may enrobe the pessary device. The overwrap can enrobe the pessary device by wrapping the pessary device along the longitudinal axis of the pessary device. The overwrap may enrobe the pessary device by rolling the pessary device along the longitudinal axis when placed inside the overwrap hollow structure. The overwrap may enrobe the pessary device by moving the pessary device along the longitudinal axis of the overwrap hollow structure. The overwrap may enrobe the pessary device by moving the overwrap hollow structure along the longitudinal axis of the pessary device.

The overwrap hollow structure may exceed the pessary device at either end in the longitudinal direction from about 0.5 mm to about 100 mm to form an overwrap excess, such as, for example, by about 0.5 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, about 10 mm, about 10.5 mm, about 11 mm, about 11.5 mm, about 12 mm, about 12.5 mm, about 13 mm, about 13.5 mm, about 14 mm, about 14.5 mm, about 15 mm, about 15.5 mm, about 16 mm, about 16.5 mm, about 17 mm, about 17.5 mm, about 18 mm, about 18.5 mm, about 19 mm, about 19.5 mm, or about 20 mm, about 20.5 mm, about 21 mm, about 21.5 mm, about 22 mm, about 22.5 mm, about 23 mm, about 23.5 mm, about 24 mm, about 24.5 mm, about 25 mm, about 30 mm, about 40 mm, about 50 mm, about 60 mm, about 70 mm, about 80 mm, about 90 mm, and up to 100 mm. The overwrap hollow structure may exceed the pessary device in the transverse axis by about 1 mm to 200 mm from the exterior surface, such as, for example 1 mm, 10 mm, 20 mm, 30 mm, 40 mm, 50 mm, 60 mm, 70 mm, 80 mm, 90 mm, 100 mm.

The overwrap hollow structure excess may be positioned inside the pessary device internal cavity. The overwrap hollow structure excess may be positioned inside the pessary device cavity using any means commonly known but not limited to, heat, vacuum, air, adhesives, mechanical means and/or combinations thereof.

The overwrap may be manipulated to conform to the pessary device. Manipulation of the overwrap may occur using one or more cords around the transverse and/or longitudinal axis of the pessary device. The cords may be tied to the pessary device. The cords may be sewn to the overwrap and/or pessary device. The cords may be shrinkable when exposed to heat or infrared. The cords may be elastic.

The one or more cords can comprise any suitable material, including for example, cotton, cellulose, rayon, polyolefins such as, for example, polyethylene or polypropylene, nylon, silk, polytetrafluoroethylene, Teflon, wax, or any other suitable materials.

The overwrap may be manipulated while covering the pessary device by anchoring at least one of the ends of the overwrap and manipulating the overwrap by rotating the device along the longitudinal axis. The overwrap may be anchored by friction, the use of adhesives, the use of heat, and/or combinations thereof.

The overwrap may be manipulated by stretching the overwrap hollow structure enrobing the pessary device and allowing it to contract to the shape of the pessary device. The overwrap may be manipulated to deform the overwrap hollow structure to match the shape of the enrobed pessary device. Manipulation and/or deformation of the overwrap may occur by any means commonly known, such as, mechanical means, force, heat, infrared, microwave, radar, ultrasound, steam, chemical reactions, and/or combinations thereof.

The overwrap may be manipulated to conform to the pessary device by creating one or more attachment points. The attachment points may be created by heat and/or adhesives. The attachment points may be located at any portion of the pessary device including the ends, along the longitudinal axis, and along a transverse axis. The attachment points may form quadrants, triangles, or any other known pattern.

The pessary device can include a withdrawal member that can comprise any suitable material, including for example, cotton, cellulose, rayon, polyolefins such as, for example, polyethylene or polypropylene, nylon, silk, polytetrafluoroethylene, Teflon, wax, or any other suitable materials.

The withdrawal member can be formed by any suitable formation method and in any suitable configuration, such as, e.g., one or more cords, strings, finger covers, ribbons, an extension of a material of the device, or combinations thereof.

The pessary device can be inserted without the use of an applicator. The pessary device can be inserted digitally using one or more of the user's fingers.

The pessary device can be inserted using an applicator that can include an insertion member and a plunger. The insertion member can have an insertion end and a withdrawal end opposite the insertion end. The insertion member also can include a barrel region adapted to contain the pessary device, and a grip region that can be an indentation region provided opposite the insertion end, such as, e.g., proximal to the withdrawal end.

The insertion member and/or plunger can be constructed from any suitable material. Suitable materials include, for example, paper, paperboard, cardboard, cellulose, such as, e.g., molded cellulose, or any combinations thereof, polyethylene, polypropylene, polybutylene, polystyrene, polyvinylchloride, polyacrylate, polymethacrylate, polyacrylonitrile, polyacrylamide, polyamide, nylon, polyimide, polyester, polycarbonate, polylactic acid, poly hydroxyalkanoate, ethylene vinyl acetate, polyurethane, silicone, derivatives thereof, copolymers thereof, mixtures thereof, or any suitable smooth plastic material. Examples of suitable materials are disclosed in, e.g., U.S. Pat. Nos. 5,346,468 and 5,558,631. Additives can be included in the material to alter or enhance certain material properties. Suitable additives include, for example, mold release agents, slip agents, surface energy modifiers, pearlescent agents, and/or any other suitable additives. The insertion member also or alternatively can be coated with a substance to give it a high slip characteristic, such as, e.g., with wax, polyethylene, a combination of wax and polyethylene, cellophane, clay, mica, and other lubricants that can facilitate comfortable insertion. Alternatively, or in addition, the insertion member can include a textured surface. Texture can be provided in any suitable manner, such as, e.g., by designing texture into or adding texture to the insertion member.

The insertion member can include a grip region, such as, for example, an indentation region. The grip region can have a plurality of three-dimensional surface elements, such as, e.g., projections, rings, ridges, ribs, embossments, depressions, grooves, and/or other gripping structures. The three-dimensional surface elements can be provided in any suitable manner, such as, e.g., by the addition of material, and/or by impressing, such as, e.g., by embossing, or compressing the surfaces. For example, the indentation region can include one or more flattened sides and/or one or more spaces for a decorative marking or a character, such as, e.g., an embossed and/or printed marking or character. In addition, or alternatively, the surfaces of the indentation region can include a material that can provide a frictional resistance for the user's fingers during the insertion of the applicator into the body. Suitable materials that can provide friction include, for example, abrasive materials, high wet coefficient of friction materials, pressure sensitive adhesives, or any combinations thereof.

The pessary device can be used daily. For example, a user can insert the pessary device, wear the pessary device for a suitable wear time, such as, for example, up to 4 hours, up to 5 hours, up to 6 hours, up to 7 hours, up to 8 hours, up to 9 hours, up to 10 hours, up to 11 hours, up to 12 hours, or up to 16 hours, or more, remove the pessary device, dispose of the pessary device, and insert a new pessary device.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of conforming an overwrap to a pessary device, the method comprising:
   a. providing a pessary device comprising a longitudinal axis, a transverse axis, and an outer surface;
   b. providing an overwrap material;
   c. prior to contacting the overwrap material with a profile sealing tool, placing a portion of the overwrap material under tension;
   d. placing the pessary device in contact with the overwrap material along a first side of the pessary device, and placing the pessary device in contact with the overwrap material along a second side of the pessary device opposing the first side, wherein the overwrap material covers at least a portion of the pessary device outer surface area;
   e. contacting the overwrap material with the sealing tool, joining the overwrap material to itself and forming part of the final overwrap; and
   f. removing the sealing tool.

2. The method of claim 1, wherein the sealing tool creates a heat seal.

3. The method of claim 1, wherein the sealing tool creates a seal comprising one or more bonds.

4. The method of claim 3, wherein the one or more bonds is created by heat, the use of adhesives, the use of friction, the use of mechanical means, and/or combinations thereof.

5. The method of claim 1, wherein the sealing tool forms a profile seal comprising bonds that have a point diameter between 0.5 mm to 2 mm.

6. The method of claim 1, wherein joining the overwrap to itself occurs with heat sealing at a temperature between 135° C. to 200° C.

7. The method of claim 1, wherein a bond is created by heat, the use of adhesives, the use of friction, the use of mechanical means, and/or combinations thereof.

8. The method of claim 1, wherein the profile sealing tool comprises an additional component that maintains a temperature below the melt temperature of the overwrap.

9. A method of conforming an overwrap to a pessary device, the method comprising:
   a. providing a pessary device comprising a longitudinal axis, a transverse axis, and an outer surface;
   b. providing an overwrap material;
   c. placing the pessary device in contact with the overwrap, wherein the overwrap material covers at least a portion of the pessary device outer surface area; and
   d. manipulating the overwrap material to conform to the pessary device using a profile seal;
   wherein manipulating the overwrap material to conform to the pessary device using a profile seal further comprises:
      a. placing a portion of the overwrap material under tension;
      b. contacting the overwrap material with a sealing mechanism, joining the overwrap material to itself on opposing sides of the device and forming part of a final overwrap; and
      c. removing the sealing mechanism.

10. The method of claim 9, wherein the profile seal comprises bonds that have a point diameter between 0.5 mm to 2 mm.

11. The method of claim 9, wherein the overwrap material is elastic.

12. The method of claim 9, wherein joining the overwrap material to itself occurs with heat sealing at a temperature between 135° C. to 200° C.

13. The method of claim 9, wherein the sealing mechanism consists of a profile sealing mold.

14. The method of claim 9, wherein the sealing mechanism creates a seal comprising one or more bonds.

15. The method of claim 14, wherein the one or more bonds is created by heat, the use of adhesives, the use of friction, the use of mechanical means, and/or combinations thereof.

* * * * *